United States Patent [19]
Bierman

[11] Patent Number: 6,132,398
[45] Date of Patent: *Oct. 17, 2000

[54] MEDICAL TUBING SECUREMENT SYSTEM

[75] Inventor: Steven F. Bierman, Del Mar, Calif.

[73] Assignee: Venetec International, Inc., San Diego, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/953,036

[22] Filed: Oct. 17, 1997

[51] Int. Cl.[7] ................................................. A61M 5/32
[52] U.S. Cl. .................. 604/174; 604/180; 128/DIG. 26
[58] Field of Search ........................... 604/174, 177–180; 128/DIG. 26

[56] References Cited

U.S. PATENT DOCUMENTS

| | | |
|---|---|---|
| D. 364,922 | 12/1995 | Bierman . |
| D. 375,355 | 11/1996 | Bierman . |
| 2,525,398 | 10/1950 | Collins . |
| 2,707,953 | 5/1955 | Ryan . |
| 3,059,645 | 10/1962 | Hasbrouck et al. . |
| 3,064,648 | 11/1962 | Bujan . |
| 3,482,569 | 12/1969 | Raffaelli . |
| 3,630,195 | 12/1971 | Santomieri . |
| 3,677,250 | 7/1972 | Thomas . |
| 3,766,915 | 10/1973 | Rychlik . |
| 3,856,020 | 12/1974 | Kovac . |
| 3,906,946 | 9/1975 | Nordstrom . |
| 3,973,565 | 8/1976 | Steer . |
| 4,020,835 | 5/1977 | Nordstrom et al. . |
| 4,057,066 | 11/1977 | Taylor . |
| 4,059,105 | 11/1977 | Cutruzzula et al. . |
| 4,129,128 | 12/1978 | McFarlane . |
| 4,161,177 | 7/1979 | Fuchs . |
| 4,224,937 | 9/1980 | Gordon . |
| 4,248,229 | 2/1981 | Miller . |
| 4,250,880 | 2/1981 | Gordon . |
| 4,316,461 | 2/1982 | Marais et al. . |
| 4,326,519 | 4/1982 | D'Alo et al. . |
| 4,362,156 | 12/1982 | Feller, Jr. et al. . |
| 4,392,853 | 7/1983 | Muto . |
| 4,397,647 | 8/1983 | Gordon . |
| 4,449,975 | 5/1984 | Perry . |
| 4,453,933 | 6/1984 | Speaker . |
| 4,480,639 | 11/1984 | Peterson et al. . |
| 4,711,636 | 12/1987 | Bierman . |
| 4,742,824 | 5/1988 | Payton et al. . |
| 4,808,162 | 2/1989 | Oliver . |
| 4,852,844 | 8/1989 | Villaveces . |
| 4,857,058 | 8/1989 | Payton . |
| 4,863,432 | 9/1989 | Kvalo . |
| 4,897,082 | 1/1990 | Erskine . |
| 4,898,587 | 2/1990 | Mera . |
| 4,919,654 | 4/1990 | Kalt . |
| 4,955,864 | 9/1990 | Hajduch . |

(List continued on next page.)

FOREIGN PATENT DOCUMENTS

| | | |
|---|---|---|
| 0064284 A2 | 4/1982 | European Pat. Off. . |
| 356683 | 7/1989 | European Pat. Off. . |
| 2381529 | of 1978 | France . |
| WO 92/19309 | 11/1992 | WIPO . |

*Primary Examiner*—Glenn K. Dawson
*Assistant Examiner*—Michael J. Hayes
*Attorney, Agent, or Firm*—Knobbe, Martens, Olson & Bear, LLP

[57] ABSTRACT

A securing system includes a simply-structured device which permits medical tubing or other elongated medical devices to be easily secured to a patient, desirably without the use of tape or needles and suturing. The securing system includes a fitting having one or more flexible arms which secure the medical tubing to the fitting. The securing system may also include a retainer having a flexible anchor pad with an adhesive bottom surface, which can be attached to the patient's skin. The fitting can be mounted to the retainer, for example, by inserting posts of the retainer through holes of the fitting. Advantageously, the securing system can be attached anywhere along the length of the tubing and can be applied to tubing of any size. Further, the system is simply to instal and easy to apply.

21 Claims, 6 Drawing Sheets

U.S. PATENT DOCUMENTS

| | | |
|---|---|---|
| 4,976,700 | 12/1990 | Tollini . |
| 5,037,397 | 8/1991 | Kalt et al. . |
| 5,073,170 | 12/1991 | Schneider . |
| 5,084,026 | 1/1992 | Shapiro . |
| 5,098,399 | 3/1992 | Tollini . |
| 5,147,322 | 9/1992 | Bowen et al. . |
| 5,156,641 | 10/1992 | White . |
| 5,192,273 | 3/1993 | Bierman et al. . |
| 5,192,274 | 3/1993 | Bierman . |
| 5,195,981 | 3/1993 | Johnson . |
| 5,266,401 | 11/1993 | Tollini . |
| 5,292,312 | 3/1994 | Delk et al. . |
| 5,304,146 | 4/1994 | Johnson et al. . |
| 5,306,243 | 4/1994 | Bonaldo . |
| 5,314,411 | 5/1994 | Bierman . |
| 5,338,308 | 8/1994 | Wilk . |
| 5,342,317 | 8/1994 | Claywell . |
| 5,344,406 | 9/1994 | Spooner . |
| 5,354,282 | 10/1994 | Bierman . |
| 5,380,293 | 1/1995 | Grant . |
| 5,403,285 | 4/1995 | Roberts . |
| 5,413,562 | 5/1995 | Swauger . |
| 5,443,460 | 8/1995 | Milusek . |
| 5,456,671 | 10/1995 | Bierman . |
| 5,468,231 | 11/1995 | Newman et al. . |
| 5,470,321 | 11/1995 | Forster et al. . |
| 5,496,282 | 3/1996 | Militzer et al. . |
| 5,496,283 | 3/1996 | Alexander . |
| 5,499,976 | 3/1996 | Dalton . |
| 5,520,656 | 5/1996 | Byrd . |
| 5,527,293 | 6/1996 | Zamierowski . |
| 5,637,098 | 6/1997 | Bierman . |
| 5,693,032 | 12/1997 | Bierman . |
| 5,722,959 | 3/1998 | Bierman . |
| B1 5,147,322 | 1/1996 | Bowen et al. . |

MEDICAL TUBING SECUREMENT SYSTEM

BACKGROUND OF THE INVENTION

1. Field of the Invention

The present invention relates to a system for securing medical tubing to a patient.

2. Description of Related Art

It is very common in the medical industry to utilize medical tubing to provide various liquids or solutions to a patient. For example, medical tubing such as an intravenous ("IV") catheter is often used to introduce fluids and medications directly into the bloodstream of a patient. In many cases, and particularly with respect to cardiac therapy, the IV catheter is introduced into a central or larger vein located close to the patient's heart. A typical catheter utilized in connection with a central vein is referred to as a "central venous catheter" ("CVC"). A venous catheter peripherally inserted into the central circulation through a vein in the arm is commonly referred to as a "peripherally inserted central catheter" ("PICC").

In these cases, long-term IV infusion typically requires that the catheter remain in place for many days. In order to secure such an IV catheter in position at the insertion site, the catheter often is provided with an integrated or a movable flexible clamp with winged extensions which are sutured to the patient's skin. In other applications, the flexible clamp is covered by a rigid box clamp, which receives the catheter/clamp combination in a friction-fit manner. The rigid box clamp and the flexible clamp have lateral, aligned holes in them, which allow the combination to be sutured to the patient's skin.

Although the box clamp securely attaches the catheter to the patient, the sutures are obviously painful and uncomfortable for the patient. Additionally, the rigid box clamp is relatively expensive and its use is limited to a catheter of a particular size. Thus, a plurality of box clamps of different sizes must be available for use with catheters of different sizes. Further, box clamps require a significant amount of time and effort to instal, increase the risk of needle-stick to the health care provider, and are difficult to use.

SUMMARY OF THE INVENTION

A need therefore exists for a simply-structured securement system that attaches medical tubing in a generally fixed position to a patient.

The present invention advantageously provides a securing system that is simple and easy to apply. Significantly, the securing system can be connected anywhere along the length of the tubing and it can be connected to tubing of any size. In addition, the present securing system is inexpensive and does not require any significant labor or effort to install. These and other advantageous are set forth in greater detail below.

One aspect of the present invention involves a securing system for attaching medical tubing to a patient. The securing system includes a fitting having at least one flexible arm adapted to engage medical tubing. The flexible arm includes at least two sides and at least a portion of one side includes an adhesive layer. The fitting also includes a coupling structure which allows the fitting to be connected to a patient.

Another aspect of the present invention includes a securing system with a fitting having at least one arm configured to engage the medical tubing, and a coupling structure to attach the medical tubing to the patient. The securing system preferably also includes retainer with a base configured to be attached to a patient. The coupling structure allows the fitting to be mounted to the retainer.

Yet another aspect of the present invention involves a securing system for attaching medical tubing to a patient. The securing system comprises a retainer including a base for receiving a fitting. Desirably a cover is coupled to the base. The cover is movable between a closed position, in which at least a portion of the cover extends over at least a portion of the base, and an open position. Preferably a latching mechanism operates between the base and the cover to releasably latch the cover to the base with the cover in the closed position. The securing system desirably also includes a fitting having at least one arm with an adhesive on one surface. The fitting and retainer also include a coupling structure which allows the fitting and retainer to be connected.

A further aspect of the present invention involves a securing system for attaching medical tubing to a patient. The securing system includes a fitting with at least one arm and a coupling structure. The securing system also includes a retainer with a base, and at least one filament extending from the base. At least one receptacle is coupled to the base and the receptacle is arranged so as to cooperate with at least one of the filaments. Each receptacle includes at least one aperture which is configured to receive the filament. The aperture inhibits retraction of the filament from the receptacle. The coupling structure allows the fitting to be mounted to the retainer.

A preferred method of attaching medical tubing to a patient involves providing a retainer including a base with at least one post extending from the base. The retainer also includes an adhesive layer to secure the retainer to the patient. The retainer is positioned on the patient, and the adhesive layer is attached to the patient. A fitting including at least one flexible arm and at least one aperture configured to engage the post is also provided. The fitting is positioned over the base to bring the aperture of the fitting in proximity with the post of the base. The fitting is mounted to the base by engaging the post with the aperture in the fitting.

Further aspects, features, and advantages of the present invention will become apparent from the detailed description of the preferred embodiments that follow.

BRIEF DESCRIPTION OF THE DRAWINGS

The above-mentioned and other features of the invention will now be described with reference to the drawings of several preferred embodiments of the present securing system. The illustrated embodiments of the securing system are intended to illustrate, but not to limit the invention. The drawings contain the following figures.

DETAILED DESCRIPTION OF THE PREFERRED EMBODIMENTS

The present embodiments of the medical tubing securing system are disclosed in the context of an exemplary central line catheter. The principles of the present invention, however, are not limited to PICCs or CVCs. Instead, it will be understood by one of skill in this art, in light of the present disclosure, that the securing systems disclosed herein can be successfully utilized in connection with other types of medical tubing or lines, including tubes for fluid communication, electrical wires and the like. For example, but without limitation, the systems disclosed herein can retain CVCs, PICCs, Foley catheters, and hemodialysis catheters; surgical drainage tubes, feeding tubes, chest tubes, and nasogastric tubes; scopes; and electrical wires or cables connected to external or implanted electronic devices or sensors. One skilled in the art may also find additional applications for the devices and systems disclosed herein. Thus, the illustration and description of the securing system in connection with a catheter is mainly exemplary of one possible application of the system.

Each of the preferred embodiments described herein employ the same basic concepts and characteristics of the medical tubing securing system, namely using a fitting to attach medical tubing to a patient. The fitting includes a coupling structure that allows the fitting to be mounted directly to the patient (i.e., sutured to the patient), or to a connector such as a retainer. The connection of the fitting and the retainer may be readily releasable for quick disconnection, or the connection may provide a secure, relatively permanent connection. Preferably, the connection of the retainer and the fitting generally inhibits relative movement between the medical tubing and the retainer in at least one degree of freedom.

To assist in the description of the components of the disclosed securing systems, the following coordinate terms are used. A longitudinal axis extends generally parallel to the elongated portion of the retainer, generally in the plane of a base of a retainer (discussed below). A lateral axis extends generally perpendicular to the longitudinal axis within the plane of the base of the retainer. A transverse axis extends generally transverse to both the longitudinal and lateral axes. In addition, as used herein, "longitudinal direction" refers to a direction substantially parallel to the longitudinal axis; "lateral direction" refers to a direction substantially parallel to the lateral axis; and "transverse direction" refers to a direction substantially parallel to the transverse axis. These coordinates are used to describe the structure and positioning of the securing system. A detailed description of the preferred embodiments now follows.

Figure 1:
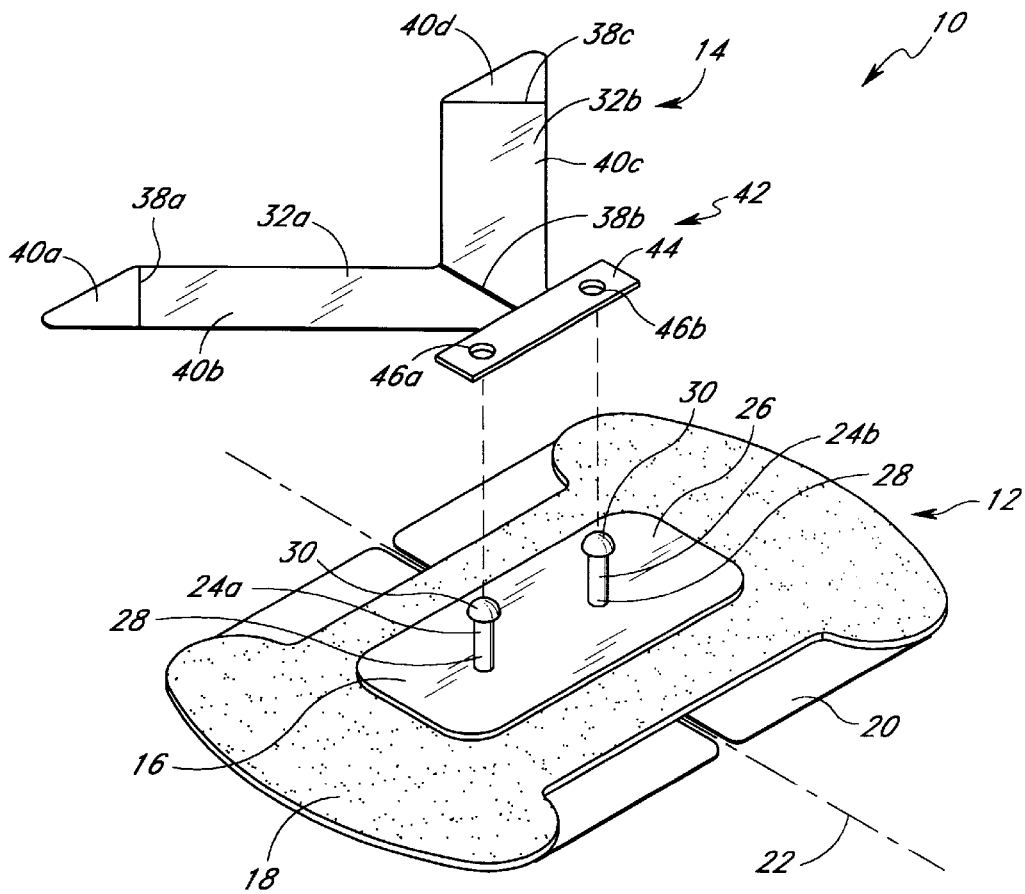
FIG. 1 is a perspective view of a securing system in accordance with a preferred embodiment of the present invention, illustrating a retainer and a fitting.

FIG. 1 illustrates a securing system 10 constructed in accordance with a preferred embodiment of the present invention. The system 10 includes fitting 14 which is configured to retain medical tubing. It will be understood by one skilled in the art that the medical tubing is used broadly to include a variety of types of medical tubing or lines. For example, without limitation, the medical tubing may include lines, passages, conduits, catheters, wires, cables and the like.

The fitting 14 desirably allows the medical tubing to be placed in the proper position relative to the patient. Advantageously, as described below, the fitting 14 may be configured to engage different types of tubing in a variety of configurations, and the fitting may be connected to any portion of and at any location along the tubing. Additionally, the fitting 14 may be attached directly to the skin of the patient, or to a retainer which is attached to a patient. The fitting 14 may be connected directly to the patient, for example by using sutures or medical grade adhesive tape. As described below, various types of retainers can also be used in conjunction with the fitting 14 to attach the medical tubing to the patient.

In a preferred embodiment, the fitting 14 is configured to be attached to a retainer 12 with a base 16. The base 16 of the retainer 12 is attached to an anchor pad 18. The base 16 desirably is secured to the anchor pad 18 by a solvent bond adhesive, such as cyanoacrylate or other bonding material. One such adhesive is available commercially as Part No. 4693 from the Minnesota Mining and Manufacturing Company ("3M").

The anchor pad 18 comprises a flexible structural layer for securing the retainer 12 to a patient's skin. The pad desirably comprises a laminate structure with an upper cellulose foam layer (e.g., closed-cell polyethylene foam), and a bottom adhesive layer. The adhesive desirably is a medical-grade adhesive and can be either diaphoretic or nondiaphoretic, depending upon the particular application. Such foam with an adhesive layer is available commercially from New Dimensions in Medicine of Columbus, Ohio. Although not illustrated, it will be understood that the retainer and/or anchor pad can include suture holes in addition to the adhesive layer to further secure the anchor pad to the patient's skin.

An upper surface of the foam layer is roughened by corona-treating the foam with a low electric charge. The roughened or porous upper surface of the anchor pad 18 improves the quality of the adhesive joint formed by the cyanoacrylate (or by another type of adhesive or bonding material) between the base 16 and the anchor pad 18. Alternatively, the anchor pad 18 can comprise a medical-grade adhesive bottom layer, an inner cellulose foam layer and an upper paper or other woven or nonwoven cloth layer.

A removable paper or plastic backing 20 desirably covers the bottom adhesive surface of the anchor pad 18 before use. The backing 20 preferably resists tearing and is divided into a plurality of pieces to ease attachment of the pad to a patient's skin. Desirably, the backing 20 is split along a center line 22 of the anchor pad 18 in order to expose only half of the adhesive bottom surface at one time. The backing 20 also advantageously extends beyond at least one edge of the anchor pad 18, as illustrated in FIG. 1, to facilitate removal of the backing 20 from the adhesive layer. Although not illustrated, the halves of the backing 20 can be formed with excess material folded downward at the center line 22 to form pull tabs. These tabs further facilitate removal of the backing and application of the anchor pad 18 to the patient.

In the illustrated embodiment, the anchor pad 18 also desirably includes a pair of opposing enlarged sections surrounding the relatively narrower center section of the anchor pad 18. As a result, the peripheral ends of the anchor pad 18 have more contact area to provide greater stability and adhesion to a patient's skin, while allowing the center section of the anchor pad 18, proximate the base 16, to cover a relatively smaller portion of the patient's skin.

The retainer 12 and the fitting 14 desirably include interacting coupling structure to couple the fitting 14 to the retainer 12. As will be clear from the disclosure below, the interacting coupling structure that mounts the fitting 14 to the retainer 12 may comprise a variety of structures. The term "mount," when used with reference to the relation between the fitting 14 and the retainer 12, does not necessarily imply that the medical tubing is immobilized or fixed. Rather, this term is meant to describe the condition in which the movement of the medical tubing relative to the retainer 12 is constrained in at least one degree of freedom (e.g., rotational, lateral, longitudinal or transverse).

As seen in FIG. 1, a portion of the interacting coupling structure on the base 16 comprises at least one post 24 which extends generally upwardly from a relatively rigid platform 26. The base 16 desirably includes two posts 24a and 24b. The base 16 can also include additional posts to suit a specific application. For example, where the retainer is designed to secure a relatively large fitting, the base can include four posts arranged at the corners of a rectangle, for greater stability. Alternatively, three posts can be used to firmly anchor a Y-site fitting. One skilled in the art will recognize the number of posts may depend upon the desired use of the securing system 10.

Each post 24 includes a shank or shaft 28 which is attached to and extends generally upwardly from the platform 26. The posts 24 can have a variety of lengths and a variety of distances between them, depending upon the particular application and the particular fitting 14 with which they are to interact to mount the medical tubing. Preferably, each post 24 desirably has a length of about 0.1 cm to 1 cm, and more preferably a length of about 0.6 mm; however, longer or shorter lengths also are possible. The posts 24 are laterally spaced at least wide enough to engage the fitting 14. Preferably, the posts 24 are spaced apart by a distance between 0.2 cm and 2 cm, and more preferably by a distance equal to about 1.2 cm. The shaft 28 of each post 24 has a diameter sufficient to perform its structural function, as described in more detail below, and depends upon the material chosen for the base 16 and shafts 28. The illustrated posts 24 preferably comprise a polymer plastic material, with a diameter between 0.5 mm and 20 mm and particularly about 10 mm.

At least one protrusion 30 extends radially outward from the shaft 28 of each post 24. As seen in FIG. 1, the protrusion 30 preferably comprises an enlarged tip or head at the end distal from the platform 26. Desirably, the protrusion 30 has a diameter of 1.1 to 1.5 times the diameter of the shaft 28. In the illustrated embodiment, the protrusion 30 has a generally hemispherical shape with a generally smooth upper surface. It will be understood that the protrusion 30 can take a variety of other shapes, such as, for example, solid or hollow conicals, arrowheads, barbs, spheres, mushroom heads, and other types of radially projecting structures. A relatively blunt end of the protrusion 30 is preferred to avoid snagging on materials such as a health care provider's latex gloves or sheets on the patient's bed.

Figure 2:
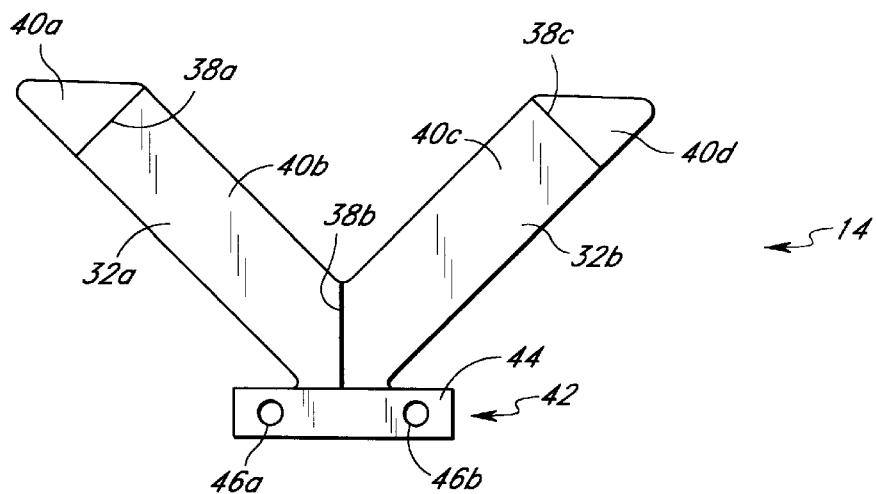
FIG. 2 is a top plan view of the fitting of FIG. 1.

FIGS. 1 and 2 illustrate the fitting 14 with two flexible arms 32a and 32b. Alternatively, as discussed below in conjunction with FIGS. 10 and 11, the fitting may have only a single flexible arm. Of course more than two arms may also be utilized, for example, depending upon the desired use of the fitting or the type of medical tubing to be attached to the fitting. The arms 32 are preferably between 2 cm and 20 cm in length and, more preferably, about 6 cm in length. Of course, any length sufficient to engage the medical tubing may be utilized.

The arms 32 are preferably constructed from a flexible material such as plastic, cloth, or paper that exhibits sufficient strength to withstand tearing or significant deformation in the context of the intended use of the fitting 14. More preferably the arms are constructed from a spun bonded olefin, paper-like material available from E.I. DuPont de Nemours, Inc. under the trade name 1079D Tyvek™, but other materials such as polyethylenes may also be suitable. The Tyvek™ preferably has a thickness of about 0.008 inch.

Figure 3:
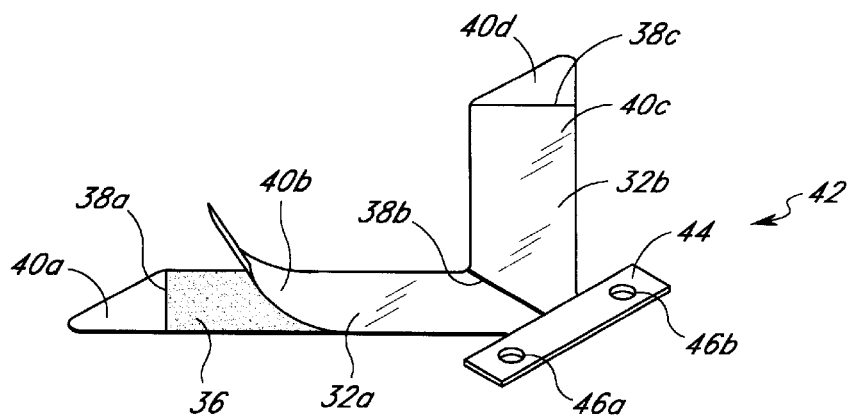
FIG. 3 is a perspective view of the fitting of FIG. 1, illustrating a portion of the removable backing layer removed to expose a portion of an adhesive layer.

At least a portion of one side of the arms 32 includes an adhesive layer 36 (shown in FIG. 3). The adhesive is desirably a medical-grade adhesive such as Part No. 9672LE by 3M. The adhesive layer 36 preferably has a thickness of about 0.005 inch, but the thickness can also be greater or smaller. The arms 32a and 32b are desirably arranged at approximately a 90° angle relative to each other, but it will be understood that the arms can be arranged at any desired angle, depending, for example, on the number of arms and the type of medical tubing to be attached to the fitting.

As best seen in FIGS. 2 and 3, a removable backing paper 40 (i.e., a release layer) desirably covers the adhesive layer 36 before use. The backing 34 preferably resists tearing and is divided into separate portions to ease attachment of the fitting 14 to the medical tubing. Desirably, the backing 40 is cut along lines 38a, 38b, 38c to form four different portions 40a, 40b, 40c, 40d to facilitate attachment of the medical tubing to the fitting 14.

The fitting 14 also includes a coupling structure 42, which preferably comprises a base 44 attached to the flexible arms 32. The base 44 is generally rectangular in configuration and is preferably constructed from a material which is more rigid than the flexible arms 32. The base 44 is preferably located proximate the intersection of the arms 32a and 32b, as shown in the accompanying figures, but the base may be connected to any portion of the arms 32. The arms 32 are preferably located at about a 45° angle relative to the base 44, but the arms can be attached at any angle relative to the base 44. The base 44 includes at least one aperture 46, and preferably two apertures 46a and 46b, but more than two apertures may also be utilized. The base 44 is preferably constructed from polyvinylchloride ("PVC") and the base 44 has a thickness of about 0.008 inch, but other materials and different thickness, depending for example upon the desired use of the fitting 14, may also be used. Alternatively, instead of using a base, the coupling structure 42 may simply comprise one or more apertures located in the arms 32 of the fitting 14.

The fittings 14 are preferably constructed using a converter process. As known in the art, a converter process may use large rolls or sheets of material to construct a laminate structure. For example, the converter process is first used to apply the adhesive layer 36 to the roll or sheet of material used to construct the flexible arm 32, preferably Tyvek™. The Tyvek™ layer, with the adhesive layer, is then cut into strips with the desired width. Alternatively, the Tyvek™ layer may be pre-cut to the desired width and then the adhesive layer 36 is applied. The base 44 of the coupling structure 42 is then securely fastened proximate one edge of the strip by means such as glue. The releasable backing layer 40 is then connected to the adhesive layer 36. The backing layer 40 is then "kiss-cut" along the lines 38a, 38b 38c to separate the adhesive layer into the desired backing portions 40a, 40b, 40c, 40d. Additionally, the backing layer 40 is "kiss-cut" proximate the connection of the coupling structure 42 to the arm 32. The "kiss-cut" cuts the backing layer 40, but not the underlying Tyvek™ layer or the coupling structure 42. The individual fittings 14 are then created by means such as stamping, punching or die casting; and then apertures 46 in the coupling structure 42 are similarly created by stamping, punching or die casting. Of course, the apertures 46 may be created before the individual fittings 14 are cut-out, or simultaneously with fittings 14. Advantageously, the converter process allows multiple fittings 14 to created at the same time, which decreases the manufacturing costs.

As discussed above, the coupling structure 42 allows the fitting 14 to be connected directly to the patient, or used with various types of retainers, such as the retainer 12 above. If the fitting 14 is used with the retainer 12, the apertures 46a and 46b are preferably configured to engage the posts 24a and 24b extending from the base 16. As shown in the accompanying figures, the apertures 46a and 46b preferably have a diameter slightly smaller or slightly larger than the protrusions 30 on the posts 24, and the apertures 46 are preferably spaced in the same general configuration and distance apart as the posts 24 extending from the base 16.

Figure 4:
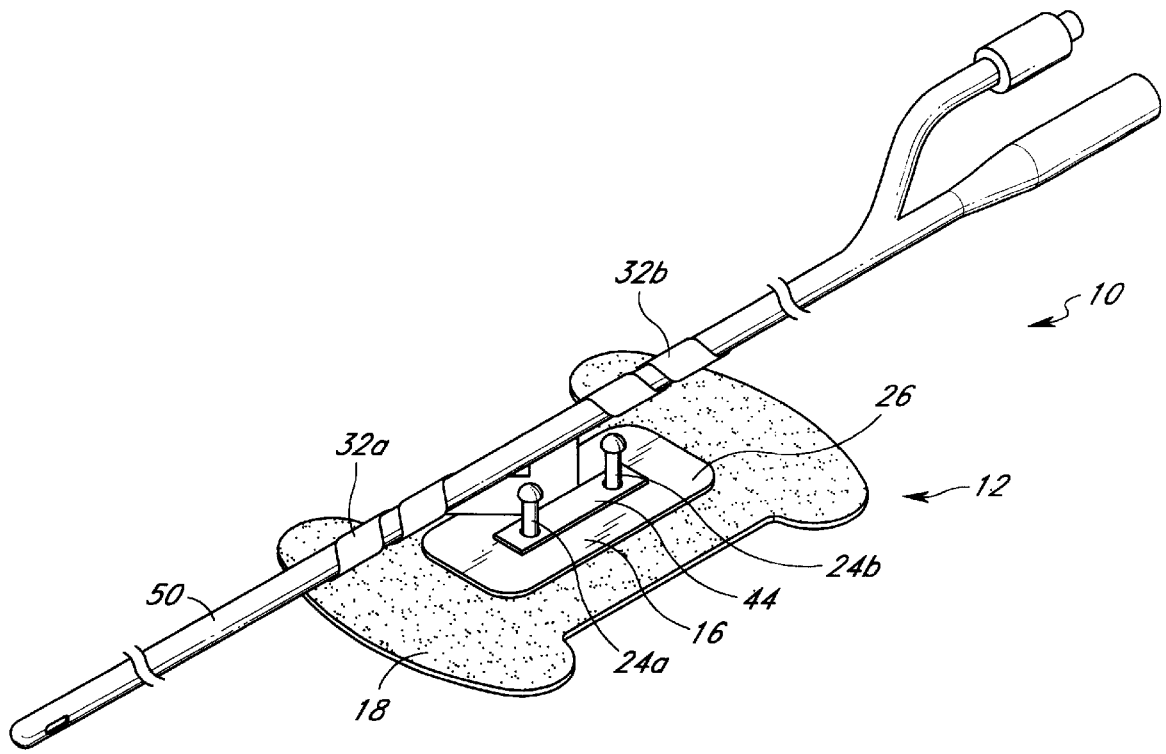
FIG. 4 is a perspective view of the fitting and retainer of FIG. 1, illustrating the fitting attached to the retainer and a preferred embodiment of attaching exemplary medical tubing to the fitting.

In operation, if the fitting 14 is being used with the retainer 12, the health care provider generally aligns the apertures 46a and 46b with the respective posts 24a and 24b. The posts 24a and 24b are then inserted through the apertures 46a and 46b. As seen in FIG. 4, the interaction between the posts 24a and 24b and the apertures 46a and 46b mounts the fitting 14 on the base 16 of the retainer 12.

FIG. 4 also illustrates the medical tubing 50 connected to the fitting 14. In particular, the medical tubing 50 is attached to the fitting 14 by wrapping the flexible arms 32 of the fitting 14 around the tubing 50 so that the adhesive layer 36 engages the tubing 50. This provides secure engagement of the tubing 50 to the fitting 14. Advantageously, the fitting 14 may be attached anywhere along the length of the tubing 50. Thus, the fitting 14 may be placed proximate either end of the tubing 50, or somewhere between the ends of the tubing. For example, if the fitting 14 is used with a catheter, the fitting may be positioned proximate the catheter or the fitting may be spaced from the catheter.

In use, as described in more detail below, for example, the health care provider removes backing portion 40b and wraps the flexible arm 32a around a portion of the medical tubing 50. The health care provider then removes backing portion 40c and wraps the flexible arm 32b around the medical tubing 50. The backing portions 40a and 40b desirably allow the health care provider to grip the distal ends of the arms 32 without contacting the adhesive layer 36. The health care provider may then remove the remaining backing portions 40a and 40b to complete attachment of the flexible arms 32a and 32b to the medical tubing 50; or the backing portions 40a and 40b may remain attached to the flexible arms 32a and 32b to facilitate removal of the fitting 14 from the medical tubing 50.

One of many possible applications for the securing system 10 includes attaching the fitting 14 to the tubing 50 so that the tubing 50 extends generally parallel to the longitudinal axis of the retainer 12. For example, as seen in FIG. 4, flexible arm 32a is wrapped around a portion of the tubing 50 in one direction (e.g., to the left) and flexible arm 32b is wrapped around another portion of the tubing 50 in an opposite direction (e.g., to the right). When the fitting 14 is attached to the retainer 12, the tubing 50 extends in the longitudinal direction relative to the retainer 12.

Figure 5:
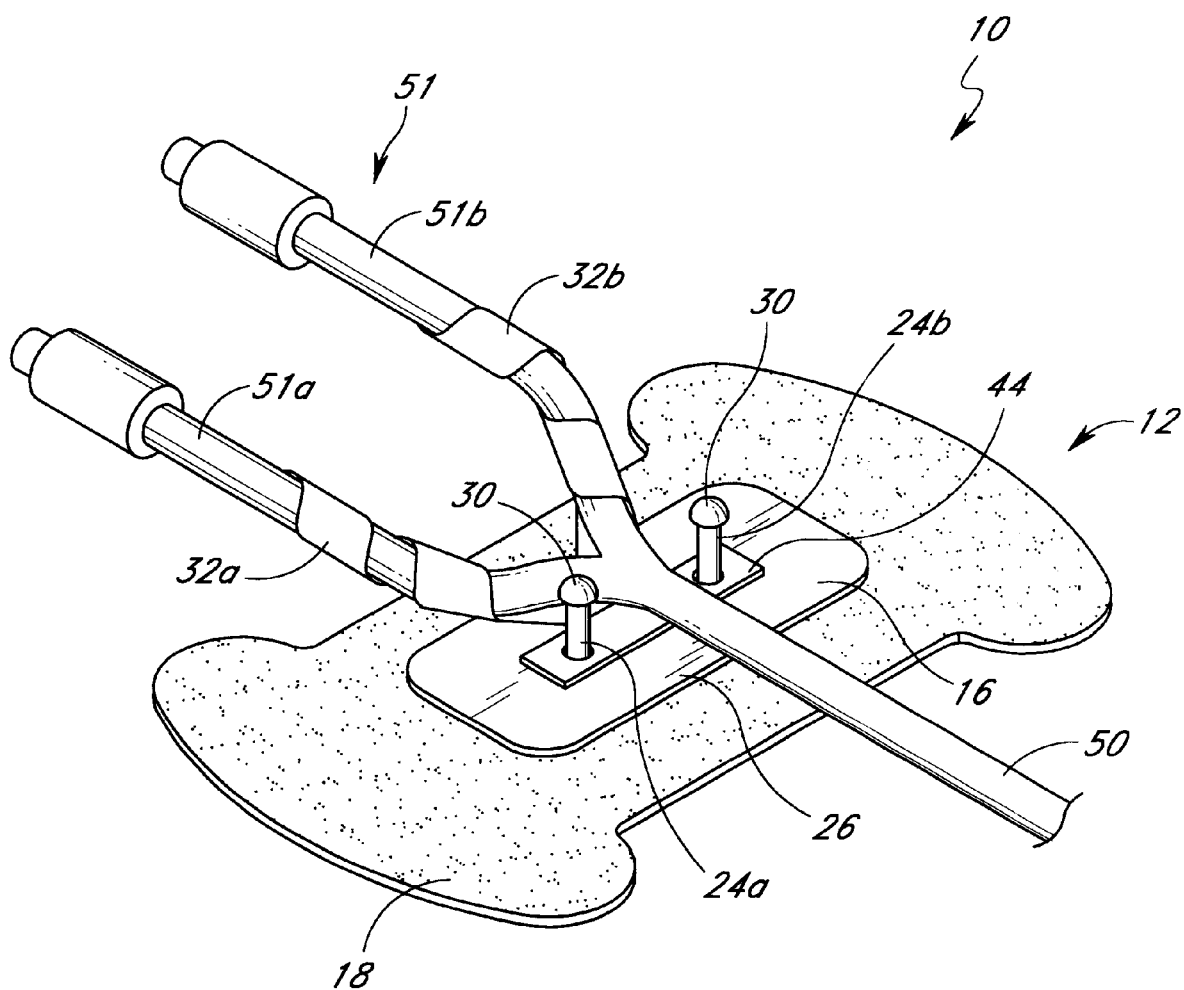
FIG. 5 is a perspective view of the fitting and retainer of FIG. 1, illustrating the fitting attached to the retainer and a preferred embodiment of attaching exemplary "Y"-type medical tubing to the fitting.

Another application includes attaching the fitting 14 to different types of medical tubing, such as Y-type tubing 51. As shown in FIG. 5, the Y-type tubing 51 is positioned with the Y-connection proximate the base 16. Flexible arm 32a is wrapped around a portion 51a of the tubing 51, and flexible arm 32b is wrapped around a portion 51b of tubing 51. Thus, the Y-type tubing 51 is securely attached to the fitting 14 by the flexible arms 32.

Figure 6:
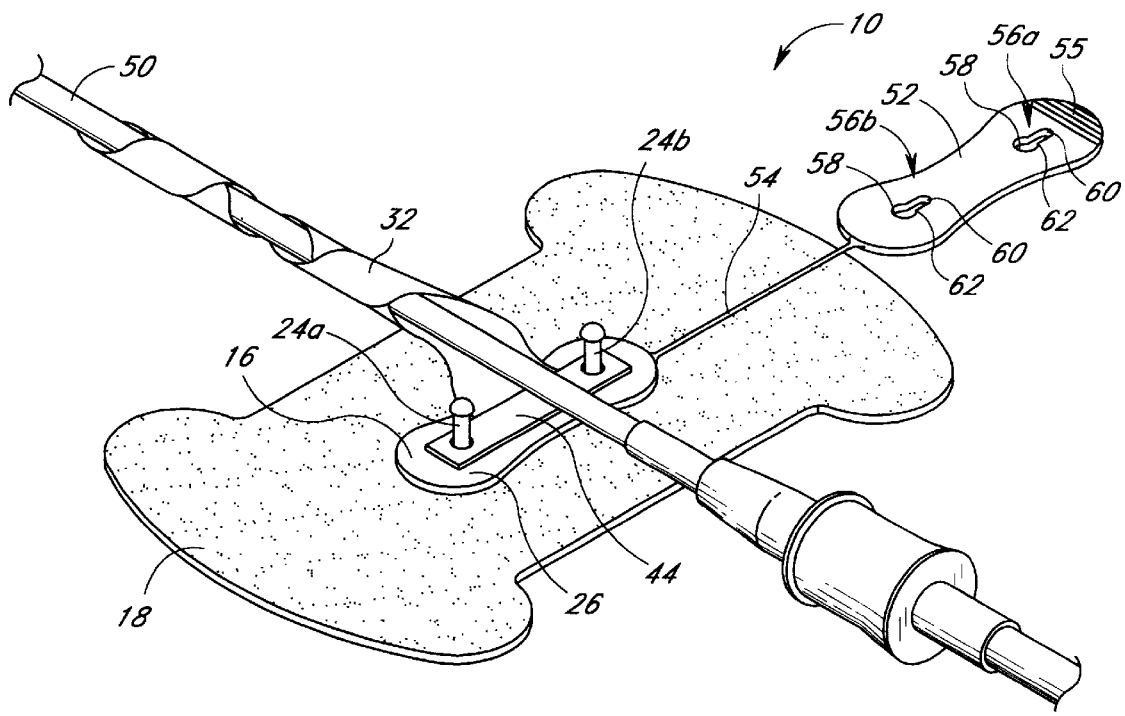
FIG. 6 is a perspective view of a securing system in accordance with another preferred embodiment of the present invention, illustrating a retainer with a cover in an open position and another preferred embodiment of attaching exemplary medical tubing to the fitting.
Figure 7:
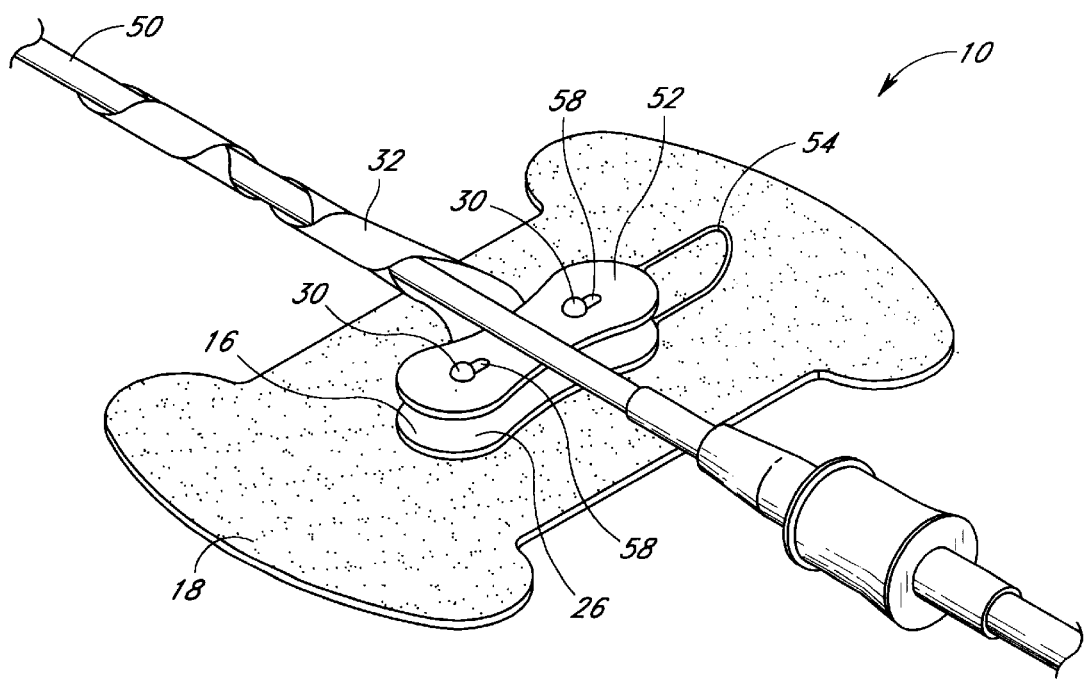
FIG. 7 is a perspective view of the fitting and retainer of FIG. 6, illustrating the cover in a closed position.

An additional application includes attaching the fitting 14 to the tubing 50 so that the tubing 50 extends generally parallel to the lateral axis of the retainer 12. For example, the Y-type tubing 51 shown in FIG. 5 extends generally in the lateral direction. Additionally, other types of tubing may extend in a generally lateral direction relative to the retainer 14. For example, as shown in FIGS. 6 and 7, both flexible arms may be wrapped around the same portion of tubing 50 so that the tubing 50 is positioned generally parallel to the lateral axis of the retainer 12. For example, flexible arm 32a may be wrapped around a portion of the tubing 50 and flexible arm 32b may be wrapped generally around the same portion of the tubing 50 so that the arms 32a and 32b overlap. Indeed, one skilled in the art will recognize the flexible arms 32 may be used in a variety of ways to attach the medical tubing 50 to the fitting 14.

One skilled in the art will understand the tubing 50 can be attached to the retainer 12 in any desired direction, for example, by shifting the orientation of the fitting 14 relative to the retainer 12. Alternatively, the positioning of the apertures 46 in the support 44 and/or the posts 24 relative to the base 16 may be altered to change the orientation of the tubing 50 relative to the retainer 12.

Another embodiment of the securing system 10 is also shown in FIGS. 6 and 7. In this embodiment, a cover 52 flexibly coupled to the base 16 by a flexible leash 54. The leash 54 can take any number of forms to mechanically connect the cover 52 to the base 16 while permitting movement of the cover 52 relative to the base 16 so as to enable engagement or disengagement of these parts, as described below. The cover 52 and leach 54 are desirably connected to the base 16 so as not to interfere with the mounting of the fitting 14.

In the illustrated embodiment, the leash 54 comprises a band of flexible material. The leash 54 desirably is integrally molded with the base 16 and the cover 52. The illustrated leash 54 has a longitudinal width of about 0.5 mm to 5 mm, desirably about 1 mm, and a similar depth or transverse dimension. The length of the leash 54 depends in part upon the height of the posts 24. The leash 54 is preferably longer than the height of the posts 24, to allow some leeway in engaging or disengaging the cover 52 with the base 16, as understood by one of skill in the art. While the leash 54 desirably is generally oblong in cross-section, as illustrated, and fixes an orientation of the cover 52 relative to the base 16, it will be understood that the leash 54 can also have a string-like (e.g., rounded) configuration and allow rotation of the cover 52 about the lateral axis.

The cover 52 is an elongated member which can be formed of the same polymer or plastic material as the base 16, and desirably is integrally molded with the base 16. The cover 52 desirably has a shape that is generally coextensive with the platform 26 of the base 16. For example, the cover 52 and platform 26 of the base 16 may be elliptical as shown in FIGS. 6 and 7. Of course, the cover 52 and platform 26 may be square, rectangular, circular, or any other desired shape. The cover 52 also can be smaller than the platform 26, however, the cover 52 should have a length at least sufficient to contact the posts 24 and a width that is at least as wide than the posts 24. The width and length of the cover 52 desirably is sufficient to securely engage the cover 52 to the posts 24. The corners of the cover 52 are also desirably rounded to avoid snagging on materials such as the latex gloves worn by the health care provider, bed sheets, etc.

As seen in FIG. 6, the cover 52 desirably includes a textured portion 55, such as that formed by longitudinal ridges at an end of the cover 52 opposite the leach 54. It will be understood that any well known form of texturing such as, for example, a roughened surface can be used in place of ridges. The textured portion improves the health care provider's grip on the cover 52.

The base 16 and cover 52 are further releasably connected by a latching mechanism. The latching mechanism permits the cover 52 to engage the base 16 in a closed position, as illustrated in FIG. 7. The cover 52 also can be disengaged from the base 16 and moved to an open position, as shown in FIG. 6. The latching mechanism includes interengaging structures formed on the base 16 and on the cover 52. In the illustrated embodiment, a portion of the latching mechanism on the base 16 is formed by the posts 24a and 24b with protrusions 30.

In particular, the latching mechanism on the cover 52 includes at least one aperture 56, and desirably includes the same number of apertures 56 as there are posts 24 extending from the base 16. In the illustrated embodiment, the cover 52 thus includes two openings apertures 56a and 56b which corresponds with the two posts 24a and 24b on the base 16. The distance between the apertures 56a and 56b is preferably between about 0.2 cm and 2 cm, and more preferably about 1.2 cm. Each aperture 56 is arranged in the cover 52 to cooperate with the corresponding post 24. It will be understood other arrangements of the latching mechanism are possible, for example where the posts are attached to the cover and the openings are formed in the base.

Each aperture 56 is defined by a central opening 58 with at least one slot 60 extending to one side, desirably longitudinally adjacent to and intersecting with the central opening 58 at a narrow waist opening 62. The central opening 58 is sized and shaped to accommodate the protrusion 30 on the post 24. The illustrated slot 60 extends in the longitudinal direction from the central opening 58, and the longitudinal axis of the slot 60 is generally parallel with the longitudinal axis of the retainer 14. It will be understood that the slots 60 in the cover 52 can extend from the central opening 58 in any direction, though both slots 60 desirably extend in the same general direction. In other arrangements, more than one slot can extend from each central opening.

The width of the illustrated slot 60 in the longitudinal direction is smaller than the central opening 58 and is smaller than the protrusion 30 on the post 24. The width of the slot 60 desirably ranges from slightly smaller to slightly larger than the diameter of the shaft 28. The interengagement between the posts 24a and 24b and the apertures 56a and 56b on the cover 52 form the latching mechanism that secures the cover 52 to the base 16. When the shaft 28 of the post 24 is positioned in the slot 60, the cover 52 can not be lifted from the base 16 in the transverse direction.

As mentioned above, the base 22, leash 54 and cover 52 desirably are integrally formed to make a unitary latching mechanism. This can be accomplished in any of a variety of ways well known to one of skill in the art. For instance, the entire retainer can be injection molded, in order to reduce fabrication costs. Additionally, features such as the leash 54 are desirably flexible. Suitable plastics which account for these considerations include polypropylene, polyethylene, and the like. Desirably, the illustrated retainer 12 comprises injection molded polyethylene or polypropylene.

As illustrated in FIG. 7, the cover 52 is latched to the base 16, with the support 44 of the fitting 14 interposed between the cover 52 and the base 16. Desirably, the cover 52 securely mounts the fitting 14 to the retainer 12. Of course, the securing system 10 does not require the use of the cover 52 or latching structure.

In order to close the cover 52, the apertures 56 of the cover 52 are aligned with the posts 24 extending from the base 16. The cover 52 is then moved toward the base 16 such that the protrusion 30 of each post 24 passes through the central opening 58 of corresponding aperture 56. The size and spacing of the apertures 56 and the posts 24 should result in an easy engagement so that only a light downward force is necessary, thereby avoiding pain or discomfort to the patient. In this position, the fitting 14 is positioned between the cover 52 and the base 16. One skilled in the art will understand the rings or other structures may be utilized to limit the travel of the cover 52 over the posts 24 so as to properly position the cover 52 on the posts 24 generally beneath the protrusions 30.

The cover 52 is then moved in the longitudinal direction (e.g., to the right in FIG. 7) so that the shaft 28 of each post 24 slides past the narrow waist opening 62 into the corresponding slot 60. Preferably, the material at the waist opening 62 and/or the shaft 28 slightly compresses as the cover 52 is moved by the health care provider. Desirably, the cover 52 is centered with respect to the base 16 when the posts 24 are engaged with the slots 60. The resulting engagement serves to retain the fitting 14 securely in place within the retainer 12. As the waist openings 62 are desirably slightly more narrow than the post shafts 28, the slots 60 provide a friction or snap fit engagement with the posts 24. The slots 60 are longitudinally more narrow than the protrusions 30, such that the cover 52 cannot be transversely lifted away from the base 16 in this position. The posts 24 of the base 16 and the slots 60 and the apertures 58 thereby form the latching structure. The latching structure allows the posts 24 to be easily inserted into the apertures 56 in one position but inhibits unintentional retraction of the posts 24 from the apertures 56 in a second position.

In operation, the tubing 50 is desirably connected to the fitting 14, for example, in any manner described above, and then the fitting 14 is mounted to the retainer 12. Of course, the fitting 14 may be first mounted to the retainer 12 and then the tubing 50 may be attached to the fitting 14. Desirably, the tubing 50 is positioned so as not to interfere with the mounting of the fitting 14 to the retainer 12. Additionally, if a cover 52 is utilized with the securing system 10, the tubing 50 and fitting 14 are preferably positioned so as not to interfere with the opening and closing of the cover 52.

Figure 8:
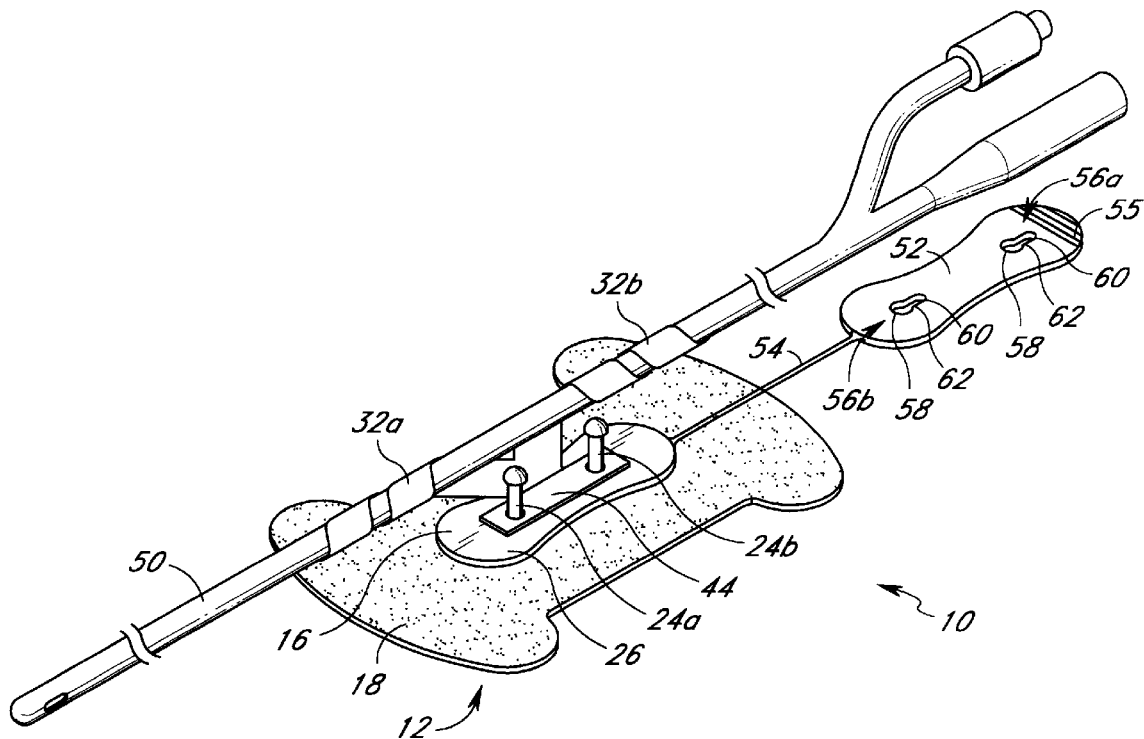
FIG. 8 is a perspective view of the fitting and retainer of FIG. 6 illustrating the cover in an open position and another preferred embodiment of attaching exemplary medical tubing to the fittings.

However, the tubing 50, arms 32 and/or leach 54 are preferably sufficiently flexible to permit mounting of the tubing 50 and fitting 14 in any position relative to the retainer 12. For example, in the embodiments shown in FIGS. 6 and 7, the tubing 50 and/or arms 32 are sufficiently flexible to allow opening and closing of the cover 52. Alternatively, as shown in FIG. 8, the tubing 50 is connected to the fitting 14 in a generally longitudinal direction so that the tubing 50 does not interfere with the closing of the cover 52.

It will be understood that, in other arrangements, the openings can instead be formed in the base, rather than the cover, and the posts formed on the cover. In such a case, each opening would comprise a partial central hole in the base, below which a hollow space is formed for receiving the heads of downward extending posts of the cover. The space would also accommodate the lateral movement of the cover (and consequent lateral movement of the posts) in order to provide engagement between the shaft of each post and a narrow slot extending from the opening. In this manner, the head of one of the posts would be captured within the hollow space below each slot. The post could not be pulled out of the hollow space because the rear side of the post head would contact the portions of the base which define the slot. Such a latching mechanism is disclosed in copending application Ser. No. 08/587,092, entitled "Catheter Anchoring System", filed on Jan. 15, 1996, in the name of Steven F. Bierman and assigned to the assignee hereof, which stands allowed as of the filing date of this application and which is hereby incorporated in its entirety by reference.

One skilled in the art will understand that the securing system 10 can be used to secure medical tubing 50 and a wide variety of other medical devices to the patient. For example, medical lines, catheters, electrical wires and the like may be attached to the posts 24 by the fitting 12. Alternatively, these devices may be directly attached to the posts 24. Specifically, box clamps, soft wing clamps and the like may be attached to the post 24. In addition, the fitting 14 and these other known medial devices can be simultaneously connected to the posts 24. In fact, the skilled artisan will find application for the present invention with any of these and many other clamp configurations. Further, an inter-line connector or adaptor, such as those used to connect the catheter to a supply, delivery or drainage line may also be utilized with the present invention.

Figure 9:
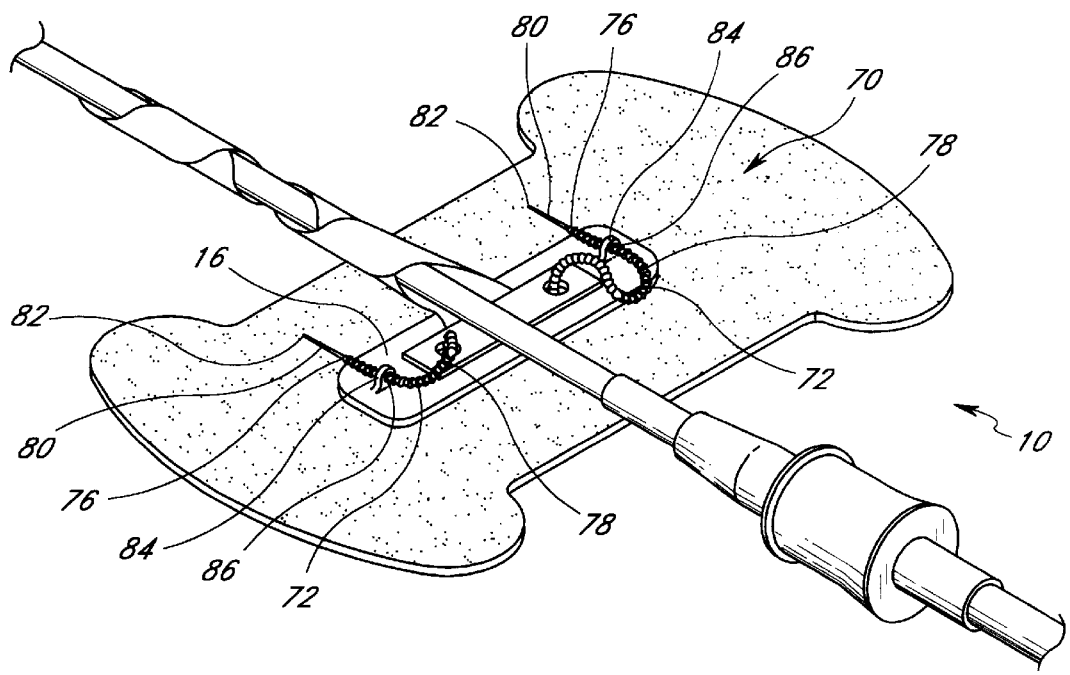
FIG. 9 is a perspective view of a securing system in accordance with yet another preferred embodiment of the present invention, illustrating a retainer and a fitting that is attached to exemplary medical tubing with a filament.

Another embodiment of the securing system 10 is shown in FIG. 9. In the illustrated embodiment, the retainer 12 includes a retention mechanism 70 comprising a pair of filaments 72 that extend from the base 16. The retention mechanism 70, of course, can include one, two, or more than two filaments, depending upon the desired use of the securing system 10. Such a retention mechanism is disclosed in U.S. Pat. No. 5,637,098 issued on Jun. 10, 1997 in the name of Steven F. Bierman, and assigned to the assignee hereof, and in copending Ser. No. 08/689,314 entitled "Catheter Securement Device," filed on Aug. 7, 1996 in the name of Steven F. Bierman, assigned to the assignee hereof, and both are incorporated by reference in its entirety.

Each filament 72 includes a fixed proximal end 74, a free distal end 76 and at least one protuberance (generally indicated by reference numeral 78). The filaments 72 can have a variety of lengths depending upon the particular application of the securing system 10. Preferably, each filament 72 has a length of about 2 to 20 cm, and more preferably about 5 cm; however, much longer or short lengths also are possible. The filaments 72 also can have a various diameter sizes depending upon the required strength of the filaments 72.

As seen in FIG. 9, each filament 72 includes a plurality of protuberances 78 arranged in series between the distal end 76 and the proximal end 74 of the filament 72. It is contemplated, however, that the filaments 72 can be configured to allow a health care provider to form the protuberance 78 in the filament 72 by tying a knot toward the distal end 76 of the filament 72. Additionally, the protuberances 78 generally have identical barb-like shapes. In the illustrated embodiment, each protuberance 78 of the filament 72 has a generally conical shape with a maximum diameter at a proximal end of the protuberance 78. Although not illustrated, the protuberances 78 can take a variety of other shapes, such as for example, hollow conical shapes, arrow shapes, or transverse rib-like shapes. The proximal end of each protuberance 78, however, desirably has a diameter which is larger than the diameter of the filament 72. As such, in the illustrated embodiment, the proximal end of each protuberance 78 forms a flat surface that lies generally transverse to a longitudinal axis of the corresponding filament 72. The proximal end surface of some or all of the protuberances alternatively can slope or project toward the distal end of the filament 72.

The filament 72 desirably includes a needle-like shaped distal portion 80 with a generally pointed, but blunt end portion 82 positioned at the distal end of the filament 72. The distal portion 80 smoothly tapers with increasing diameter from the blunt end portion 82 toward the distal-most protuberance 78. The diameter of the distal portion 80 at a point adjacent the distal-most protuberance 78 desirably equals the diameter of the filament 72 proximal to the protuberances 78.

The retention mechanism 70 also includes at least one and preferably a plurality of receptacles 84 positioned on the base 16. Each receptacle 84 is arranged on the base 16 to cooperate with at least one filament 72, as discussed below. Each receptacle 84 also includes an aperture 86 configured to engage at least a portion of a filament 72.

The receptacles 84 receive the distal ends 76 of the filaments 72 in a manner permitting the insertion of the filament 72 into the receptacle 84, but generally inhibiting the retraction of the filament 72 from the receptacle 84. For this purpose, the corresponding filament 72 and receptacle 84 include interengaging structure that allows the filament 72 to be easily inserted into the receptacle 84 in one direction with a first degree of force but prevents retraction of the filament 72 when a same or greater degree of force is applied to the filament 72 in the opposite direction. A larger degree of force is required to retract the filament 72 from the receptacle 84.

In the embodiment illustrated in FIG. 9, the interengaging structure between the corresponding filament 72 and the receptacle 84 comprises the protuberances 78 on the filaments 72 and apertures 86 of the receptacles 84. The receptacle 84 preferably facilitates insertion of the filament 72 from both sides of the receptacle.

The diameter of the aperture 86 is preferably at a minimum at the center of the width of the receptacle 84. The minimum diameter desirably is larger than the maximum diameter of the filament distal portion 80, but smaller than the maximum diameter of the protuberances 78. The receptacle 84 and/or the protuberances 78 of the associated filaments 72 are preferably configured such that a wall of the receptacle 84 about the aperture 86 and/or the protuberances 78 deflect to allow the larger diameter protuberances 78 to pass through the smaller diameter aperture 86 of the receptacle 84. Once the protuberance 78 passes through the small end of the aperture 86, the protuberance 78 and receptacle 84 spring back to inhibit retraction of the protuberance 78 through the aperture 86.

As shown in FIG. 9, each filament 72 and corresponding receptacle 84 are positioned proximate to each other on the base 16. The filaments 72 and receptacles 84 desirably are arranged so that the filaments 72 are spaced about the same distance apart as the posts 24 shown in FIGS. 1–8. Specifically, the filaments 72 are spaced apart by a distance between 0.2 cm and 2 cm, and more preferably by a distance equal to about 1.2 cm.

The base 16, filaments 72 and receptacles 84 of the retention mechanism 70 desirably are integrally formed together. This can be accomplished in any of a variety of ways which will be well known to one of skill in the art. For instance, the entire retention mechanism 70 can be integrally molded of plastic or nylon by injection molding. The retention mechanism 70 desirably is secured to the anchor pad 18 by means of a solvent bond adhesive. A suitable adhesive is available commercially from 3M, Part No. 4693.

In operation, the health care provider desirably inserts the filament 72 through the aperture 46 of the fitting 14 and then through the receptacle 84. As understood from FIG. 9, the filament 72 has sufficient length to extend through the aperture 46 and through the receptacle 84. The health care provider likewise inserts the second filament 72 through the aperture 46 in the fitting 14 and through the receptacle 84. The health care provider pulls both filaments 72 tight to draw the support 44 of the fitting 14 against the base 16 of the retainer 12. Excess filament length can be severed or cut distal to the receptacle 84. The taut filaments 72 prevent the fitting 14 from moving transversely away from the base 16 and from sliding either longitudinally or laterally over the base 16. In this manner, the securing system 10 assists maintaining the medical tubing 50 in a secure position.

When removal of the fitting 14 becomes necessary, the health care provider carefully removes any insertion site dressings which cover the securing system 10 and carefully twists the filaments 72 at a point near the proximal end 74 of the filament 72 using a blunt hemostat, so as to break or sever the filament. The fitting 12 then can be lifted from the base 16.

Figure 10:
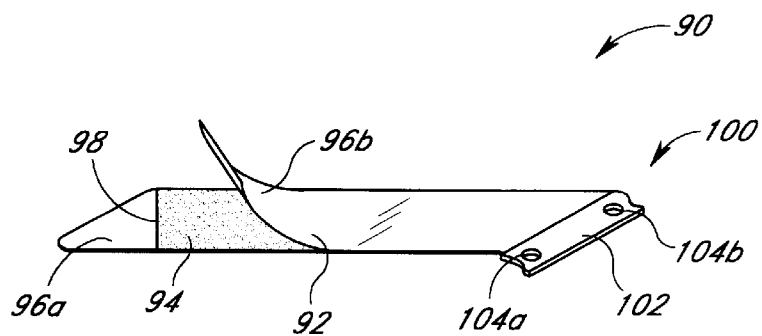
FIG. 10 is a perspective view of a fitting in accordance with another preferred embodiment of the present invention, illustrating a portion of the removable backing layer removed to expose a portion of an adhesive layer.
Figure 11:
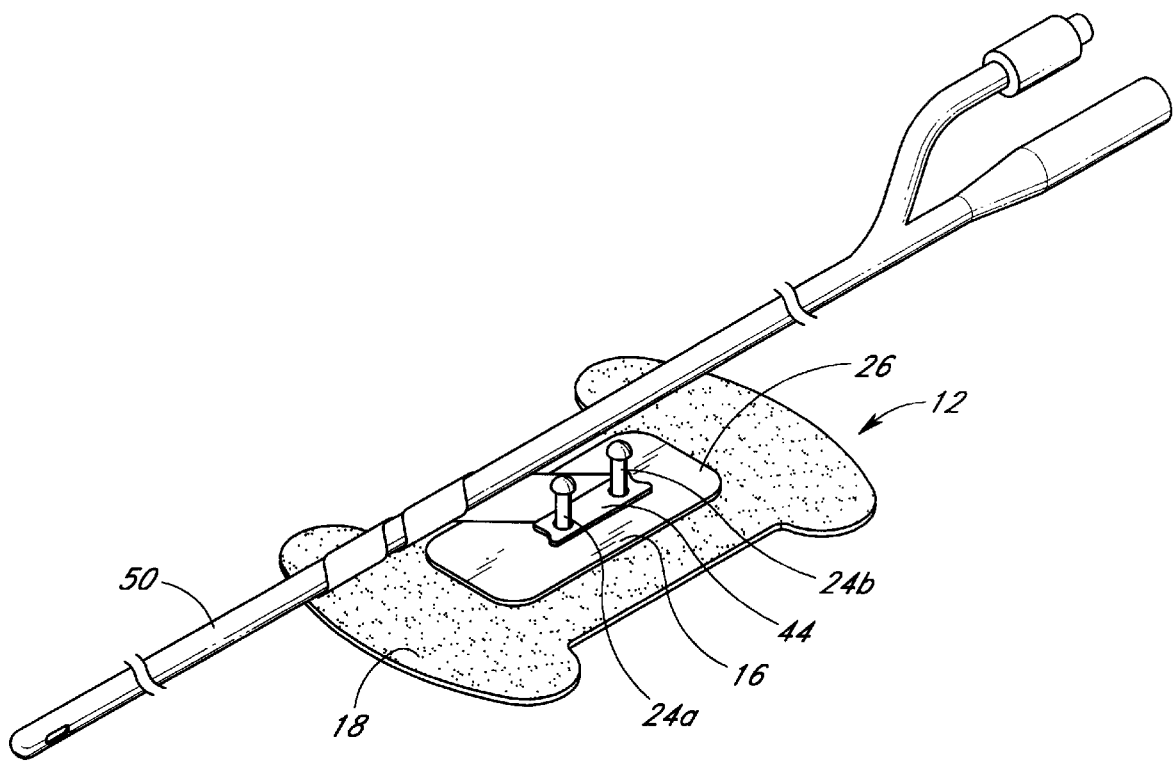
FIG. 11 is a perspective view of the fitting of FIG. 10, illustrating the fitting attached to a retainer and a preferred embodiment of attaching exemplary medical tubing to the fitting.

As shown in FIGS. 10 and 11, in another preferred embodiment of the present invention, a securing system 10 comprising a fitting 90 with a flexible arm 92 which is used to engage the medical tubing. The arm 92 is preferably between 2 cm and 20 cm in length and, more preferably, about 6 cm in length. Of course, the arm 92 may have any desired length sufficient to engage the medical tubing. As described above, the arm 92 is desirably constructed from a flexible material such Tyvek™, and at least a portion of one side of the arm 92 includes an adhesive layer 94, preferably a medical-grade adhesive such as Part No. 9672LE by 3M. A removable backing layer 96 desirably covers the adhesive layer 94 before use. The backing layer 96 preferably resists tearing and is divided into separate portions to ease attachment of the fitting 90 to the medical tubing. Desirably, the backing layer 96 is cut along line 98 to form two different portions 96a and 96b to facilitate attachment of the medical tubing to the fitting 90.

The fitting 90 includes a coupling structure 100 which comprises a generally rectangular structure 102 with two apertures 104a and 104b. The arm 92 is desirably attached to the coupling structure 100 at approximately a 60° angle, but the arm can be arranged at any desired angle, depending, for example, on the type of medical tubing to be attached to the fitting 90. The coupling structure 100 desirably allows the medical tubing to be attached to the patient. As described above, the coupling structure 100 can be sutured in place, or it can be connected to various coupling structures. Preferably, the apertures 104a and 104b are configured to engage the posts 24a and 24b of the retainer 12 described above. Of course, the coupling structure 100 can have different shapes, sizes and number of apertures, for example, depending upon the type of coupling structure being used to connect the fitting 90 to the patient. As seen in FIG. 11, exemplary medical tubing 50 is attaching to the fitting 90 by wrapping the flexible arm 92 around the tubing so that the adhesive layer 94 engages the tubing. This provided secure engagement of the tubing 50 to the fitting 90.

In operation, similar to that described above, the health care provider removes backing layer 96b and wraps the arm 92 around a portion of the medical tubing 50. The health care provider then removes backing layer 96a to complete attachment of the arm 92 to the tubing 50, or the backing portion 96a may remain attached to the arm 92 to facilitate removal of the fitting 90 from the tubing 50. The health care provider may then suture the coupling structure 100, for example, to the patient or connect it to various coupling structures, such as the retainer 12 discussed above.

In use, the health care provider selects a site in which the fitting 14 will be located. For use with CVCs and PICCs, for example, the fitting 14 is desirably positioned in the vicinity of the catheter insertion site. The health care provider then cleanses and prepares the anticipated site according to well known methods. The fitting 14 may be directly attached to the patient's skin, for example, by suturing. Alternatively, the fitting 14 may be used in conjunction with a connector such as the retainer 12 described above. In this case, the health care provider peels away a portion of the backing layer 20 from the adhesive surface of the anchor pad 18, properly locates the pad 18 on the patient, and presses the exposed adhesive against the patient's skin to secure a portion of the anchor pad 18 to the patient. The remaining portion of the backing layer 20 is then removed, and the remaining portion of the anchor pad 18 is adhered to the patient's skin. The medical tubing 50 is then attached to the fitting 14 and retainer 12 in accordance with any of the preferred embodiments described above.

When removal of the medical tubing becomes necessary, the sutures may be cut or removed to allow the fitting 14 to be removed from the patient's skin, or the fitting 14 may be removed from the posts 24 of the base 16. For example, in accordance with the embodiments shown in FIGS. 4 and 5, the posts 24 are cut or severed to allow the fitting 14 to be removed. Alternatively, in the embodiment shown in FIGS. 6–8, the cover 52 is slid longitudinally desirably with force sufficient to compress the cover material at the waist openings 62, so that the protrusions 30 on the posts 24 are once again aligned with the central openings 58. The cover 52 can then be easily lifted transversely from the base 16. With the retainer 12 thus unlatched, the fitting 14 can also be removed. Further, as shown in FIG. 8, the filaments 72 may be cut or twisted off between the proximal ends 74 and the corresponding receptacles 84 to allow removal of the fitting 14 from the retainer 12.

The medical tubing 50 secured by the fitting 14 can then be changed or cleaned and replaced, without requiring a new retainer 12 be attached to the patient. Of course, if the medical treatment is completed and there is no need to reuse the retainer 12, the health care provider can release the fitting 14 from the retainer 12 in the manner described above and the fitting 14 is then removed from the base 16. To remove the anchor pad 18, the health care provider lifts an edge of the pad 18 and gently strokes the undersurface with an alcohol swab while slowly but continuously lifting the edge. The anchor pad 18 can be peeled from the patient's skin in this manner. The health care provider then cleanses and prepares skin using well known hospital or agency protocols.

The skilled artisan will appreciate that the securing systems disclosed herein have great versatility in securing a wide variety of medical articles to a patient. Securing systems similar to those shown in the attached figures and described herein can be utilized to secure devices of various shapes and sizes. Moreover, these securing systems can be utilized with or without an associated cover. This securing system can also be used with a great many medical devices with suture holes which can be fitted over the retainer posts disclosed herein. Other devices can be modified to include such holes. Other arrangements to secure a medical article to the posts, either between the posts or adjacent to a single post, will be readily apparent to those skilled in the art in light of the disclosure herein.

Alternatively, one of skill in the art will readily appreciate that the disclosed securing systems can be modified, without departing from the spirit of the invention, to mount and retain existing medical devices. For example, the securing system can be adapted to clamp existing Y-joint adapters, or to directly mount a catheter or other medical line. Desirably, any such modified mounting structure would inhibit longitudinal and lateral movement of the device or medical line. Transverse movement is inhibited by closure of the retainer with the device or line sandwiched between the base and the cover.

Although not illustrated, the securing system can be adapted for use in an system which includes a safety loop. An anchor pad larger than the pad 18 can mount both a retainer and a separate tube clip. The medical tubing mounted by the retainer can also be secured less tightly to the tube clip, with an adequate amount of slack in the line between the retainer and the clip. The clip and the resultant slack are desirably located between the retainer and the catheter insertion site, for example.

If movement by the patient causes a sudden pull upon the medical tubing, the tubing slips within the tube clip and the slack length or "safety loop" of the tube is pulled through the clip. Friction between the clip and the sliding tube absorbs some of the force and some of the force causes a slight pull on the adhesive pad, functioning as a warning to the patient to cease the undesirable movement.

When using a retainer in accordance with the above disclosure, no painful, invasive or time-consuming sutures or other extensive procedures involving medical sharps (e.g., suture needles) are necessary to secure medical tubing to a patient. In addition, the flexible anchor pad absorbs much of the force incurred in the installation or removal of the retainer and the fitting, thereby providing greater comfort for the patient.

The present invention, when used in conjunction with a retainer, provides a sterile (or non-sterile), tight-gripping, needle-free way to secure medical tubing to a patient. The securing systems eliminate accidental needle sticks, suture wound site infections and scarring because sutures are not required. In addition, the retainers can be used with any of a wide variety of catheters, tubes, wires, and other medical articles to provide universal securement using one style of retainer. Also, patient comfort is enhanced and application time is decreased with the use of the present retainer.

Advantageously, these securing systems allow the same retainer to be used more than once on the same patient at the same location. That is, a first medical device can be mounted to the retainer. When the function of the first medical device is accomplished, the first medical device is removed, and a second medical device can be mounted to the same retainer.

Although this invention has been described in terms of certain preferred embodiments and suggested possible modifications thereto, other embodiments and modifications apparent to those of ordinary skill in the art are also within the scope of this invention. Accordingly, the scope of the invention is intended to be defined only by the claims which follow.

What is claimed is:

1. A fitting for securing a medical tubing to a patient comprising at least one flexible arm, the flexible arm having two sides, at least a portion of one of the sides including an adhesive layer arranged to make contact with the medical tubing and to attach the flexible arm to the medical tubing, and a fitting coupling structure connected to the flexible arm to attach the fitting to the patient, the fitting coupling structure including a pair of apertures for attaching the coupling structure to the patient and the at least one flexible arm being attached to the fitting coupling structure independent of the pair of the apertures.

2. The fitting of claim 1 further comprising two flexible arms joined in a generally V-shaped configuration.

3. The fitting of claim 2, wherein the fitting coupling structure is constructed from a material more rigid than the flexible arms, and the fitting coupling structure is connected proximate the intersection of the two flexible arms.

4. The fitting of claim 3, wherein the pair of apertures extends completely through the fitting coupling structure.

5. The fitting of claim 4, wherein the apertures are sufficiently closely spaced from an edge of the fitting coupling structure so as to allow the fitting to be sutured to the patient.

6. The fitting of claim 4, wherein the apertures are sized and configured to accept one or more posts to allow the fitting to be mounted to a retainer.

7. The fitting of claim 1, wherein the fitting coupling structure is constructed from a material more rigid than the flexible arm, and the fitting coupling structure is connected proximate one end of the flexible arm.

8. The fitting of claim 7, further comprising one or more apertures extending through the fitting coupling structure.

9. The fitting of claim 8, wherein the apertures are sufficiently closely spaced from an edge of the fitting coupling structure so as to allow the fitting to be sutured to the patient.

10. The fitting of claim 8, wherein the apertures are sized and configured to accept one or more posts and allow the fitting to be mounted to a retainer.

11. The fitting of claim 1, wherein the flexible arm extends from the fitting coupling structure at an acute angle relative to a line passing through the centers of the pair of apertures.

12. The fitting of claim 1, wherein the diameter of each of the pair of apertures is smaller than a width of the flexible arm.

13. A fitting for attaching a medical tubing to a patient, the fitting comprising: at least one flexible arm comprised of a first layer of generally flexible material configured to extend around a portion of the medical tubing, and a second layer covering at least a portion of the first layer, the second layer comprising a medical-grade adhesive and being positioned to contact at least a portion of the medical tubing to allow the fitting to be attached to the medical tubing, and a fitting coupling structure including two or more apertures for attaching the coupling structure to the patient, at least the first layer of the one or more flexible arms connected to the fitting coupling structure independent of the two or more apertures.

14. The fitting of claim 13, further comprising a third layer releasably attached to the second layer, wherein the third layer comprises a releasable backing layer.

15. The fitting of claim 13, wherein the apertures are sufficiently closely spaced from an edge of the fitting coupling structure so as to allow the fitting to be sutured to the patient.

16. The fitting of claim 13, wherein the apertures are sized and configured to accept one or more posts and allow the fitting to be mounted to a retainer.

17. The fitting of claim 13, wherein the fitting coupling structure is constructed from a material that is more rigid than the flexible first layer.

18. The fitting of claim 13, wherein the diameter of the apertures is smaller than a width of the flexible arm.

19. A method of attaching medical tubing to a patient, comprising the steps of:

providing a fitting including one or more flexible arms, each of the flexible arms having two sides and an outer end, at least a portion of one of the sides including an adhesive for attaching the flexible arm to the medical tubing, and a fitting coupling structure connected to the flexible arms, the fitting coupling structure including one or more apertures to couple the medical tubing to the patient;

wrapping the arm about the medical tubing to attach the fitting to the medical tubing with the other end of the arm adhered to the medical tubing; and securing the fitting to the patient in the desired location using the one or more apertures by inserting a structure through the aperture, the structure being attached to the patient.

20. A fitting for securing a medical tubing to a patient comprising a pair of flexible arms joined in a generally V-shape configuration having an inner edge that defines an inner vertex between the flexible arms, and having a fitting coupling structure, said fitting coupling structure being at a location spaced apart from the inner vertex with each arm extending outward from a base of the V-shaped configuration, each flexible arm having two sides, at least a portion of one of the sides including an adhesive layer arranged to make contact with the medical tubing and to attach the flexible arm to the medical tubing, and a fitting coupling structure connected to and extending entirely across a length of the base of the V-shaped configuration, the fitting coupling structure being more rigid than the flexible arms so as to reinforce the base of the V-shaped configuration.

21. The fitting of claim 20, wherein the inner vertex formed an angle of about ninety degrees between the flexible arms.

* * * * *